US00PP16243P3

(12) United States Plant Patent
Meilland

(10) Patent No.: US PP16,243 P3
(45) Date of Patent: Feb. 7, 2006

(54) FLORIBUNDA ROSE PLANT NAMED 'MEIWHIFLO'

(50) Latin Name: *Rosa hybrida*
Varietal Denomination: Meiwhiflo

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 141 days.

(21) Appl. No.: 10/727,539

(22) Filed: Dec. 5, 2003

(65) Prior Publication Data

US 2005/0125867 P1 Jun. 9, 2005

(51) Int. Cl.
*A01H 5/00* (2006.01)

(52) U.S. Cl. ..... Plt./144

(58) Field of Classification Search ..... Plt./144
See application file for complete search history.

*Primary Examiner*—Anne Marie Grunberg
*Assistant Examiner*—Annette H Para
(74) *Attorney, Agent, or Firm*—Burns, Doane, Swecker & Mathis, LLP

(57) ABSTRACT

A new and distinct variety of rose plant of the Floribunda Class is provided which abundantly forms attractive very double starkly brilliant white blossoms that well retain their coloration upon maturity. The growth habit is upright bushy. Very dense dark green semi-glossy foliage is formed that contrasts nicely with the blossom coloration. The plant develops well following budding and grafting. Good disease resistance is displayed. The new variety is well suited for forming attractive ornamentation in the garden or for cut flower production.

4 Drawing Sheets

Botanical/commercial classification: *Rosa hybrida*/Floribunda Rose Plant.
Varietal denomination: cv. 'Meiwhiflo'.

SUMMARY OF THE INVENTION

The new variety of *Rosa hybrida* Floribunda rose plant was created by artificial pollination wherein two parents were crossed which previously had been studied in the hope that they would contribute the desired characteristics. The female parent (i.e., the seed parent) of the new variety was the product of the cross of the 'Korbin' variety (non-patented in the United States) and the 'Korresia' variety (U.S. Plant Pat. No. 3,509). The 'Korresia' variety sometimes is known as the 'Fresia' variety or the 'Friesia' variety. The male parent (i.e., the pollen parent) was the 'Jacjem' variety (U.S. Plant Pat. No. 5,001). The 'Jacjem' variety sometimes is known as the 'Sun Flare' or 'Sunflare' variety. The 'Korbin' variety has been marketed under the ICEBERG trademark, and the 'Korresia' variety has been marketed under the SUNSPRITE trademark. The parentage of the new variety can be summarized as follows:

('Korbin'×'Korresia')×'Jacjem'.

The seeds resulting from the above pollination were sown and small plants were obtained which were physically and biologically different from each other. Selective study resulted in the identification of a single plant of the new variety.

It was found that the new variety of Floribunda rose plant of the present invention possesses the following combination of characteristics:

(a) exhibits an upright bushy growth habit, (b) forms in abundance in clusters attractive very double starkly brilliant white blossoms that well retain their coloration upon maturity, (c) forms very dense dark green semi-glossy foliage, (d) exhibits good disease resistance, and (e) is well suited for forming attractive ornamentation in the garden or for cut flower production.

The new variety well meets the needs of the horticultural industry. It is particularly well suited for growing outdoors or for the production of cut flowers under greenhouse growing conditions.

The new variety can be readily distinguished from its parental varieties. More specifically, the 'Korbin' variety forms blossoms having considerable fragrance. The 'Korresia' variety forms deep yellow blossoms, and 'Jacjem' variety forms medium yellow blossoms.

Additionally, the new variety of the present invention can be readily distinguished from the 'Jaclace' (U.S. Plant Pat. No. 4,848) and 'Meideweis' (U.S. Plant patent application Ser. No. 11/002,621, filed Dec. 3, 2004) white-flowered Floribunda varieties. The 'Jaclace' variety sometimes is designated FRENCH LACE. When compared to the 'Jaclace' variety, the new variety of the present invention forms smaller and purer white blossoms with no hint of color, and at the end of the growing season commonly displays a shorter growth habit. When compared to the 'Meideweis' variety, the new variety of the present invention lacks the strong fragrance that is exhibited by the 'Meideweis' variety, and displays a larger growth habit.

The new variety has been found to undergo asexual propagation at West Grove, Pa. and at Wasco, Calif. by budding and grafting. Asexual propagation by the above-mentioned methods as performed in Pennsylvania and California has shown that the characteristics of the new variety are strictly transmissible from one generation to another. Good plant development is displayed regardless of the mode of asexual propagation.

The new variety has been named the 'Meiwhiflo' variety and is being marketed under the SEPTEMBER MOURN trademark.

BRIEF DESCRIPTION OF THE PHOTOGRAPHS

The accompanying photographs show as nearly true as it is reasonably possible to make the same in color illustrations of this character typical specimens of the plant parts of the new variety. The rose plants of the new variety were two years of age and was photographed during October 2003 while growing on 'Dr. Huey' rootstock at Wasco, Calif. Dimensions in centimeters are included at the bottom of each photograph.

DETAILED DESCRIPTION

Figure 1:
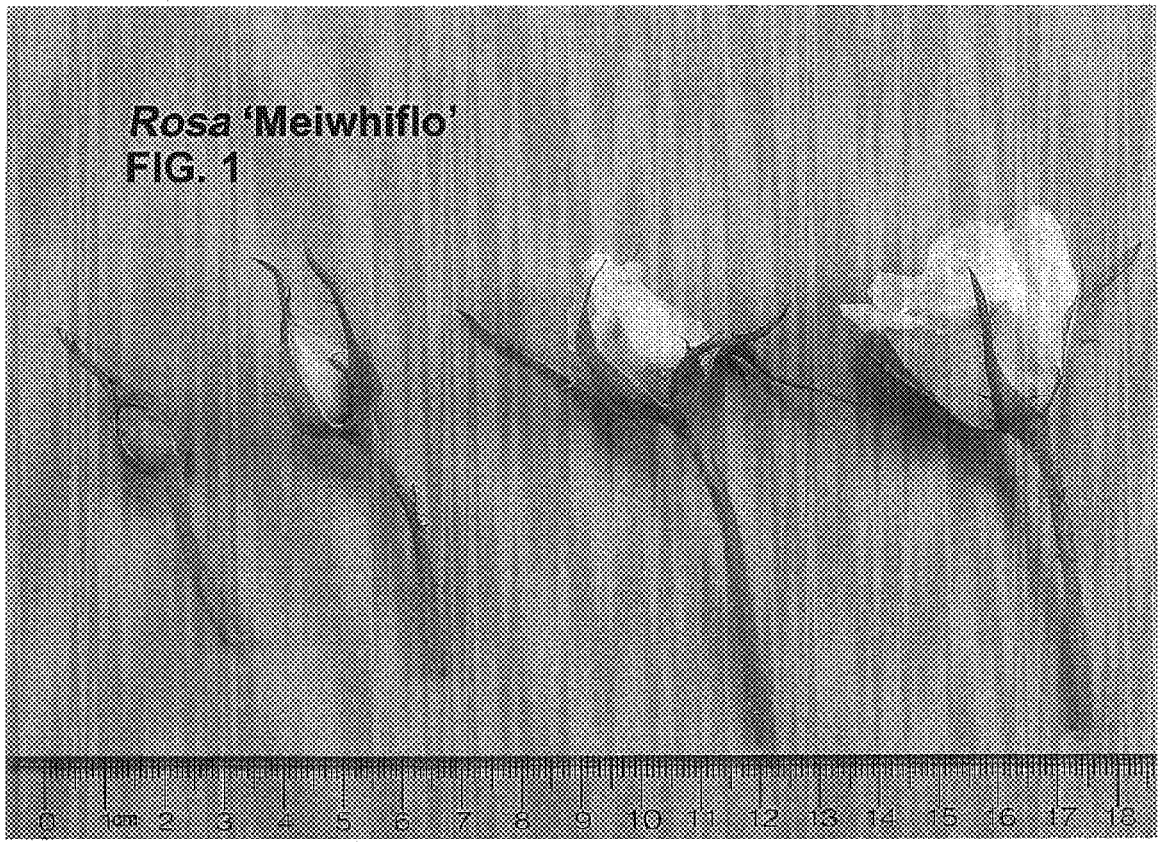
FIG. 1 illustrates a series of four flower buds in progressive stages of opening with a tight unopened bud being shown at the left and a flower in the course of opening at the right.
Figure 2:
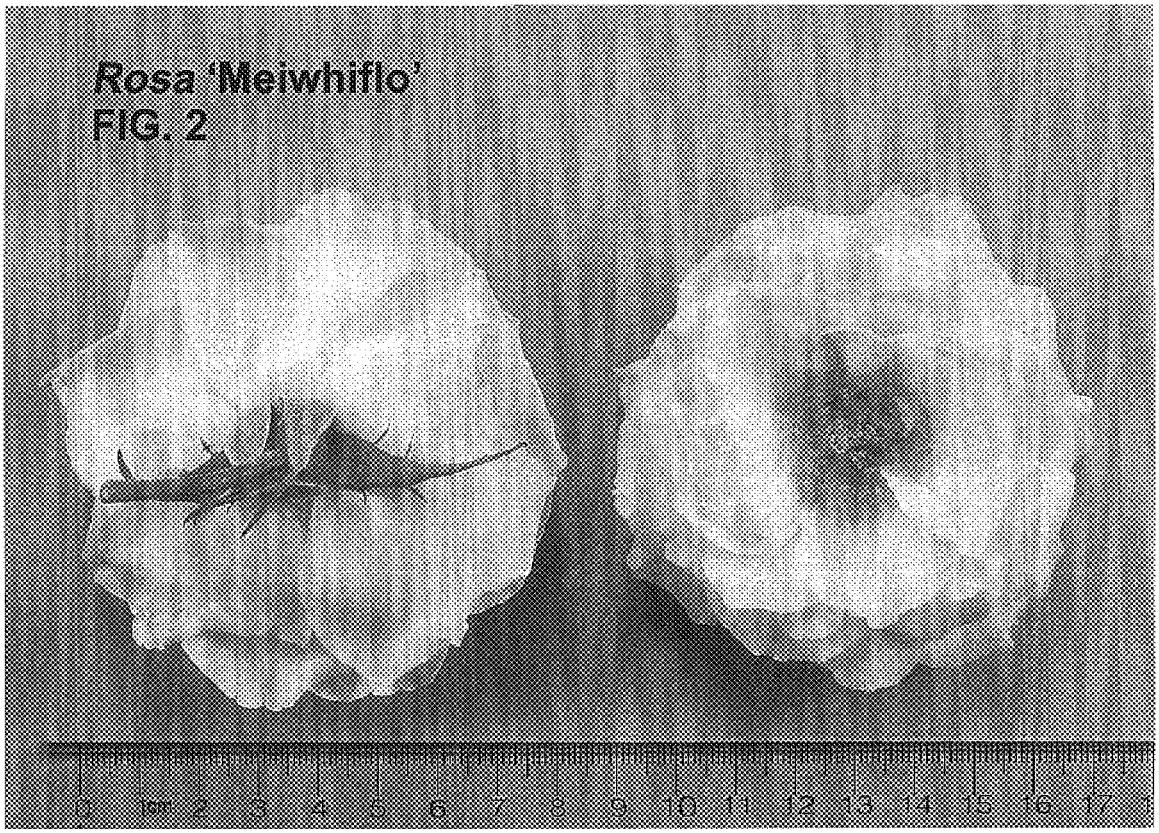
FIG. 2 illustrates open flowers with the reverse being shown at the left and the obverse at the right.
Figure 3:
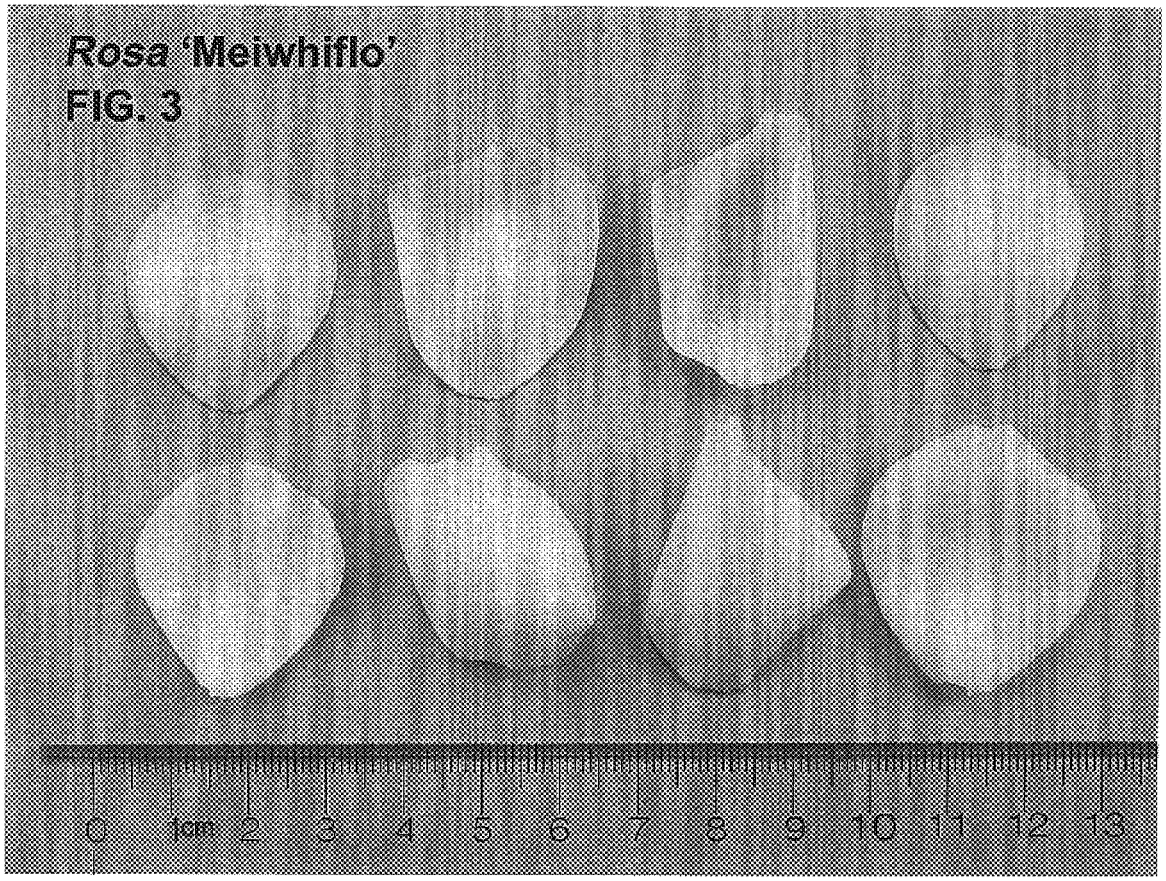
FIG. 3 illustrates typical petals. The reverse side of the petals is shown above and the obverse side below.
Figure 4:
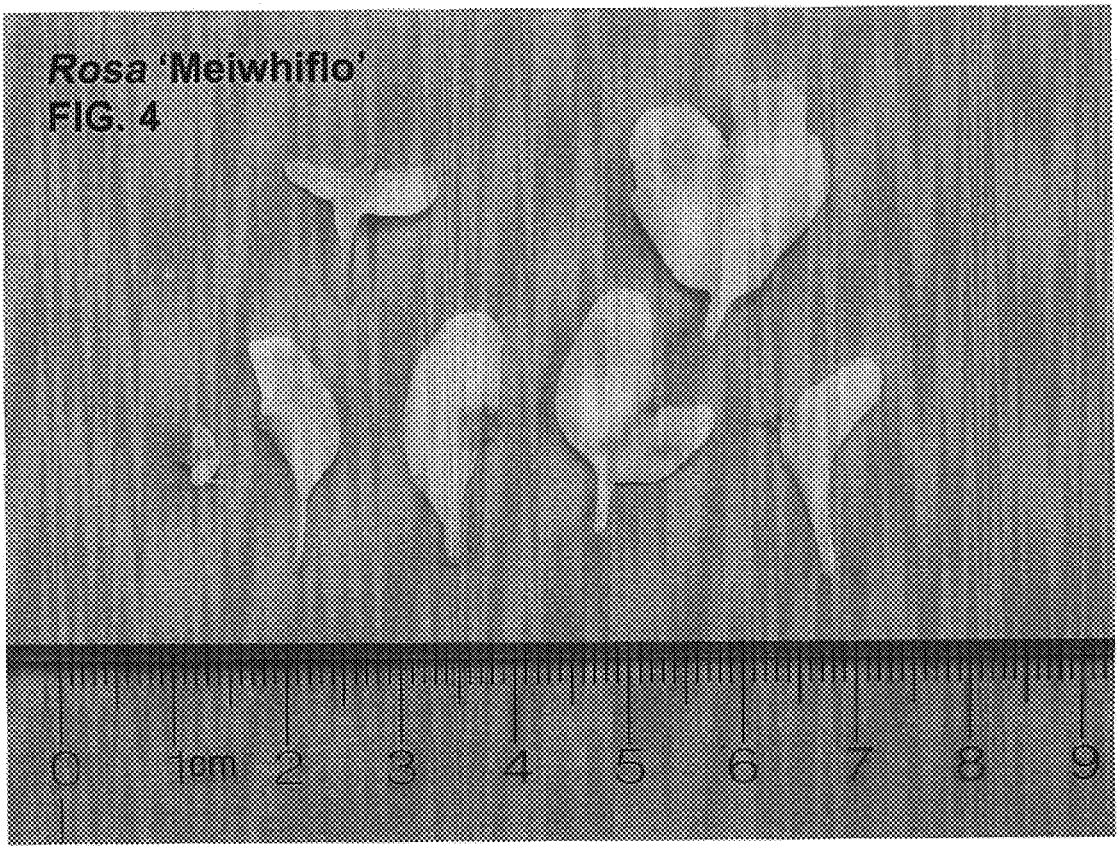
FIG. 4 illustrates representative sizes and shapes of the petaloids that commonly are displayed.

The chart used in the identification of the colors is that of The Royal Horticultural Society (R.H.S. Colour Chart). The description is based on the observation of two-year-old specimens of the new variety which were observed during October 2003 while growing on 'Dr. Huey' rootstock at Wasco, Calif.

Class: Floribunda.

Plant:

*Height.*—Approximately 100 to 120 cm on average at the end of the growing season.

*Width.*—Approximately 60 to 80 cm on average at the end of the growing season.

*Habit.*—Upright bushy.

Branches:

*Color.*—Adult wood: Green Group 137B with some lightening to and through Green Group 137C and Green Group 138A.

*Thorns.*—Size: commonly measure approximately 8 mm from the base to the tip, approximately 6 mm in height, and approximately 2 mm in width. Number: commonly, approximately 13 thorns are present per cane on average. Color: near Grey-Brown Group 199A.

Leaves:

*Arrangement.*—Alternate and odd-pinnately compound.

*Size.*—The size varies widely within and between leaves of different leaflet numbers. A mature three-leaflet leaf commonly is approximately 8 to 11.5 cm (approximately 9.5 cm on average) in length, and approximately 7 to 10.5 cm (approximately 8.5 cm on average) in width. A mature five-leaflet leaf commonly is approximately 11 to 16 cm (approximately 14 cm on average) in length, and approximately 9.5 to 14 cm (approximately 12 cm) in width. A mature seven-leaflet leaf commonly is approximately 9.5 to 18 cm (approximately 14 cm on average) in length, and approximately 8.5 to 13 cm (approximately 10 cm on average) in width.

*Leaflets.*—Number: 3 and more commonly 5 and 7. Shape: typically broadly elliptical to elliptical, occasionally oval to somewhat narrowly elliptical. Apex: abruptly acuminate to acute to broadly acute to occasionally obtusus cum acumine (blunt with a point terminating abruptly in a round end, the middle of which is suddenly lengthened into a point). Base: cuneate to broadly cuneate to almost broadly rounded. Margin: serrulate to occasionally biserrulate to serrate to occasionally biserrate, with the teeth commonly being very small near the base and larger at the upper one-half of each leaflet. Venation: pinnate, reticulate. General appearance: very dense, dark green, and semi-glossy. Terminal leaflet size: from a mature three-leaflet leaf 4 to 7 cm (approximately 5.5 cm on average) in length, and approximately 3 to 4.5 cm (approximately 3.5 cm on average) in width. From a mature five-leaflet leaf approximately 5 to 7.5 cm (approximately 6.5 cm on average) in length, and approximately 3 to 5 cm (approximately 4.2 cm on average) in width. From a mature seven-leaflet leaf approximately 3 to 6.5 cm (approximately 5 cm on average) in length, and approximately 2.5 to 5 cm (approximately 3.7 cm on average) in width. Color (adult foliage): upper surface: between Green Group 139A and Yellow-Green Group 147A. under surface: near Green Group 137C.

Inflorescence:

*Number of flowers.*—Typically approximately 1 to 5 per inflorescence.

*Peduncle.*—Commonly approximately 2.5 to 6.5 cm (approximately 4.5 cm on average) in length, and approximately 2.5 to 3.6 mm (approximately 3 mm on average) in diameter.

*Sepals.*—Five in number, lanceolate commonly with a few foliaceous extensions, and rarely a sepal is found having substantially the same coloration as the petals.

*Buds.*—Shape: narrow ovoid. Size: when the first sepal is reflexed the diameter is approximately 14 to 15.5 mm (approximately 15 mm on average).

*Flower.*—Form: very double and cup-shaped when mature. Diameter: approximately 6 to 9 cm (approximately 7.5 on average) when fully open. Overall appearance: stark bright white with a very light green hue when first opening. Color when fully open: upper surface: near White Group 155D at the upper edge, moving towards the petal base the predominant color shifts to near White Group 155A and then shades towards and through Green-White Group 157D, Group 157C, 157B, and 157A in the direction of the petal base. The veins tend to be darker and commonly are near Yellow-Green Group 145C and 145D. Under surface: primarily near White Group 155D but somewhat brighter and whiter, with some shading towards and through Green-White Group 157D, 157C, 157B, and 157A towards the center and in the direction of the petal base. Stability of coloration: very good with coloration commonly being well maintained upon full maturity. Petal configuration: typically broadly to narrowly obovate. Petal number: ranges widely from approximately 27 to 49 under typical growing conditions with an average of approximately 36. Petal arrangement: rosulate. Petal apex: typically abruptly acuminate to broadly acute to truncate to occasionally emarginate. Petal base: commonly narrowly to broadly cuneate to broadly rounded. Petal texture: glabrous, membranaceous, relatively thin and semi-translucent. Petal size: commonly approximately 25 to 45 mm (average approximately 36 mm) in length, and approximately 20 to 50 mm (average approximately 32 mm) in width. Petaloids: commonly approximately 1 to 8 (approximately 4 on average) per bloom. Fragrance: not noticeable to very slight. Pistil number: approximately 80 to 125 (approximately 102 on average). Stamen number: commonly approximately 110 to 160 (approximately 130 on average). Anthers: commonly approximately 1.2 to 2.8 mm (average approximately 2.2 mm) in size.

Development:

*Blooming.*—Typically cyclic.

*Aptitude to bear fruit.*—None observed.

*Resistance to diseases.*—Good with respect to black spot and powdery mildew.

The new 'Meiwhiflo' variety has not been observed under all possible environmental conditions to date. Accordingly, it is possible that the phenotypic expression may vary somewhat with changes in light intensity and duration, cultural practices, and other environmental factors without variance of the genotype.

I claim:

1. A new and distinct variety of Floribunda rose plant characterized by the following combination of characteristics:

(a) exhibits an upright bushy growth habit, (b) forms in abundance in clusters attractive very double starkly brilliant white blossoms that well retain their coloration upon maturity, (c) forms very dense dark green semi-glossy foliage, (d) exhibits good disease resistance, and (e) is well suited for forming attractive ornamentation in the garden or for cut flower production;

substantially as herein shown and described.

* * * * *

Rosa 'Meiwhiflo'

0 cm 2 3 4 5 6 7 8 9 10 11 12 13 14 15 16 17 18

*Rosa* 'Meiwhiflo'

*Rosa* 'Meiwhiflo'

0
1cm
2
3
4
5
6
7
8
9
10
11
12
13

Rosa 'Meiwhiflo'

0
1cm
2
3
4
5
6
7
8
9